United States Patent [19]

Clark, Jr. et al.

[11] Patent Number: 5,408,883
[45] Date of Patent: Apr. 25, 1995

[54] REMOTELY OPERATED DIAGNOSTIC TUBE SAMPLING DEVICE AND METHOD OF SAMPLING

[75] Inventors: William G. Clark, Jr., Murrysville Boro; Warren R. Junker, Monroeville; James A. Begley, Pittsburgh; Richard J. Jacko, Forest Hills; William A. Byers, Penn Hills Township, Allegheny County, all of Pa.

[73] Assignee: Westinghouse Electric Corporation, Pittsburgh, Pa.

[21] Appl. No.: 896,014

[22] Filed: Jun. 9, 1992

[51] Int. Cl.⁶ .................. G01N 1/08; G01N 27/82; G01N 29/04; G01N 29/24
[52] U.S. Cl. ......................... 73/601; 73/623; 73/633; 73/643; 73/864.41; 324/220; 324/226; 376/249; 376/260; 29/890.031; 29/334
[58] Field of Search ............ 73/620, 622, 623, 865.8, 73/592, 621, 632, 634, 866.5, 86, 87, 864.41, 7, 643, 601, 633; 324/243, 220-222, 226-229, 232, 234-240, 242, 262; 376/252, 249, 261, 200, 260; 175/78; 165/11.1, 11.2; 104/138 G; 29/26 A, 890.031, 526.4, 526.2, 402.06, 34 R, 33 T

[56] References Cited

U.S. PATENT DOCUMENTS

| | | |
|---|---|---|
| 4,079,701 | 3/1978 | Hickman et al. .................. 122/382 |
| 4,406,856 | 9/1983 | Wilkins et al. ...................... 376/260 |
| 4,790,065 | 12/1988 | Cooper, Jr. et al. ................. 29/723 |
| 4,811,759 | 3/1989 | Billoué ................................ 138/89 |
| 4,916,282 | 4/1990 | Chamming's et al. ............. 219/69.2 |
| 4,955,235 | 9/1990 | Metala et al. ......................... 73/601 |
| 5,089,684 | 2/1992 | Griffaton ......................... 219/121.63 |
| 5,212,363 | 5/1993 | Minue ................................. 219/75 |

FOREIGN PATENT DOCUMENTS

| | | | |
|---|---|---|---|
| 2573332 | 11/1984 | France ........................... 29/890.031 |
| 59-77393 | 5/1984 | Japan .................................. 29/33 T |

OTHER PUBLICATIONS

+Translations Provided With Foreign Patent Documents.

Primary Examiner—Hezron E. Williams
Attorney, Agent, or Firm—Daniel P. Cillo

[57] ABSTRACT

A robotic sampling device (32) for cutting part of a tube wall (12) for sampling, containing a cutting head (36), a retrieval assembly (38) and a drive mechanism (40), is used to cut a window or hole (60) in the tube wall (12) and retrieve the tube wall sample (56), where the sample can be mounted onto a separate tube for testing the physical properties of the cut wall portion, and where a video probe (62) and the like can be passed through the window (60) to monitor conditions near the support plates (14) and tube sheets (16).

17 Claims, 3 Drawing Sheets

FIG. 3
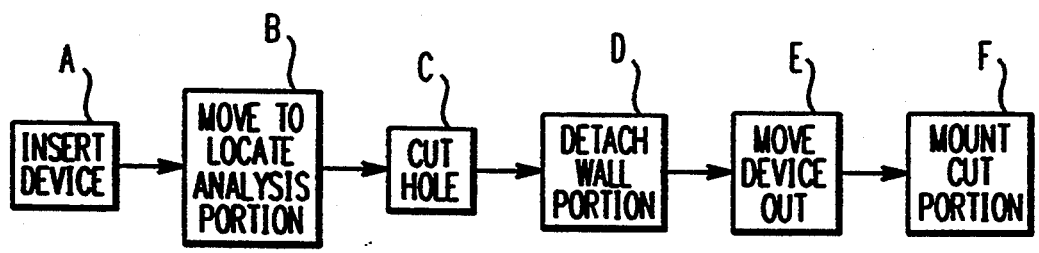
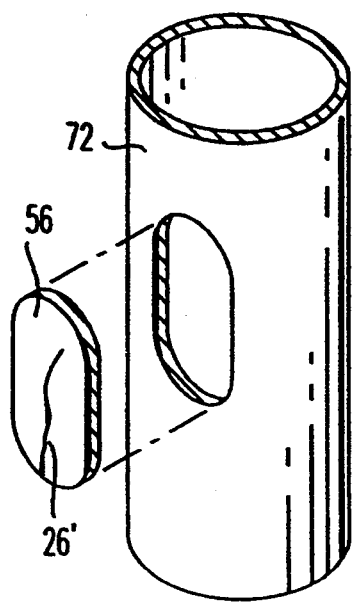
FIG. 4A
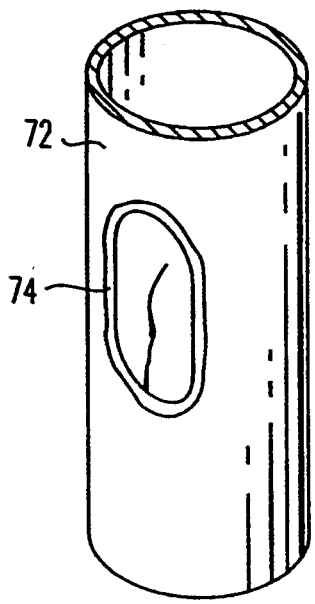
FIG. 4B
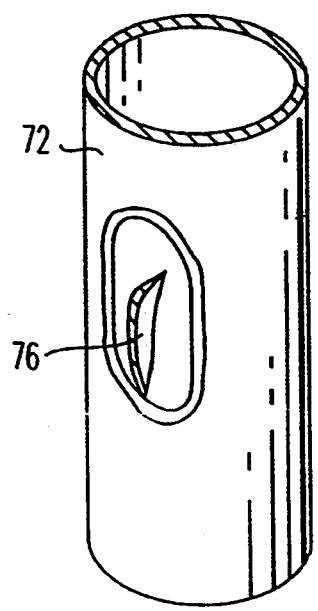
FIG. 4C

REMOTELY OPERATED DIAGNOSTIC TUBE SAMPLING DEVICE AND METHOD OF SAMPLING

BACKGROUND OF THE INVENTION

The successful long term performance of metal tubes in structures such as heat exchangers and steam generators depends strongly on operation, maintenance and repair options dictated by performance monitoring. Because of the nature of the application, on-line tube condition monitoring is not practical, and tube assessment is limited to periodic inspection with remote visual and nondestructive examination devices delivered from inside the tubing. In the area of pipeline and storage tank monitoring, a combination pulsing magnetic reluctance coil and ultrasonic transducer, has been used to measure wall thickness and to determine the presence of pits, as taught in U.S. Pat. No. 4,418,574 (Flournoy). Eddy current probe systems generating a plurality of frequencies to detect flaws at different depths in metallic conduits was taught in U.S. Pat. No. 4,855,677 (Clark, Jr. et al.). A variety of ultrasonic probe carriers for nondestructive inspection of long lengths of tubes are also known and taught in U.S. Pat. No. 4,189,944 (Day) and U.S. Pat. No. 4,388,831 (Sherman).

U.S. Pat. Nos. 4,856,337 and 4,955,235 (both Metala et al.) taught a probe carrier system for combined ultrasonic and eddy current inspection of small tubes, primarily metal heat exchanger tubes of steam generators. In these two inventions, the apparatus included a housing which was insertable within the tube to be inspected, and a rotatably mounted probe carrier, where the probes were ultrasonic emitters, and where a pancake eddy current probe was also included for inspection by means of an electromagnetic field. A system for driving such an inspection probe helically within a steam generator tube was taught in U.S. Pat. No. 4,992,735 (Cullen et al.) and U.S. Pat. No. 5,025,215 (Pirl).

The assessment of service induced localized tubing degradation such as intergranular attack and stress corrosion cracking, and the accurate prediction of remaining life requires very sophisticated nondestructive examination, followed eventually by the removal or "pull" of a full tubing cross-section sample which can be examined in the laboratory. This tube pull sample is only available through a sequence of extremely complicated remote cutting and retrieval procedures.

A method of electrical discharge machining for cutting and removal of inside repair liners and tube sections of steam generator tubes, in order to check the stability of the liner under operating conditions, has been taught in U.S. Pat. No. 4,916,282 (Chamming's). The tubing sample is often damaged during the removal procedure making subsequent analyses more complicated. In addition, once a cross-section sample has been removed, the tube involved is removed from service by plugging and no remedial action is possible.

In another area, sled type cutting devices used to re-establish side, branch connections of known location to underground sewer pipe or other buried fluid conduits which have been newly, correctively lined with plastic pipe, by means of pre-programmed pivoting cutting heads, where a video camera permitted observation of the interior of the sewer pipe, are taught in U.S. Pat. No. 4,577,388 (Wood). An improvement of this device is taught in U.S. Pat. No. 5,088,553 (Ralston et al.), where lights are included with the video camera and lateral side branches are precisely located by monitoring return signals from a microwave transmitter/receiver on the cutting device, to precisely operate a rotary cutter head. However, neither ultrasonic nor infrared inspection, to determine where the side connections were located, were considered feasible. Neither of these cutting devices relate to small tubes, and while both cut through plastic pipe, neither can diagnose problems such as pits or cracks in metal tubes nor capture a sample for analysis.

Precision, non-destructive machining of small interior samples from the inside of pipes for retrieval and inspection, has been taught in U.S. Pat. No. 4,845,896 (Mercaldi). There, a section of the tube was sampled by a linearly moveable cutting-sampling apparatus, mounted on wheels and skids, without cutting all the way through the tube wall, utilizing a moveable semi-hemispherical cutter, and leaving a shallow dimple up to about 0.6 mm deep in the interior tube wall. U.S. Pat. No. 4,925,621 (Muth et al.), also taught a linearly moveable cutting-sampling apparatus capable of cutting an interior portion of a tube to a depth of about 0.1 mm and capturing it for analysis. Two curved cutters were used. The tube was not cut all the way through. A first assembly removed an interior surface oxide layer and a second assembly then removed a curved sidewall sample to avoid sharp edges and stress concentration. These inventions solved a number of sampling problems. However, the sample removed in both inventions was very thin, and capable of only limited testing, and neither assembly could selectively locate a tube wall portion of interest, where corrosion, pitting or cracking was diagnosed by the cutting-sampling apparatus itself.

There is a need for a diagnostic sampling apparatus which would be able to diagnose where defects occur in the walls of small metal tubing, and cut away a large interior tube section without also causing retrieval difficulties or requiring removal of the tube from service. It would also be extremely valuable if a pluggable "window" were created through the tube wall after sample capture, allowing various probes to additionally monitor exterior tube conditions near tube sheets or tube support regions, electromagnetically, ultrasonically or visually. It would also be extremely valuable if the sample were large enough to be weldable to a surrogate tube after removal, to permit leak rate and burst testing. It is one of the objects of this invention to provide such an improved, diagnostic/sampling/monitoring combination cutting apparatus, and to provide a method of testing removed samples.

SUMMARY OF THE INVENTION

Accordingly, the invention resides in a remotely operated diagnostic tube sampling device, movable within a metal tube to be sampled, characterized by having: (A) an emitter and a receiver at least one of electromagnetic fields and ultrasonic waves capable when inserted in a metal tube to be sampled of locating defects in the metal tube wall; (B) a cutting head capable of cutting a hole completely through said metal tube to provide a sample; (C) a retrieval assembly capable of engaging said sample and detaching it; and (D) an associated driving mechanism capable of moving the sampling device within the tube length.

Preferably, at least one eddy current probe will be utilized to emit electromagnetic alternating fields and accurately position the cutting head, and the cutting head will contain a preshaped, elliptical, electric discharge machining electrode or similar tube cutting device. A suction cup, such as a vacuum cup, preferably disposed within the cutting head, can be used to capture the sample cut from the tube wall to provide a "window" through the tube. A variety of visual devices or probes, or machining tools could be mounted on and extendable from the sampling device to be inserted through the window, to in-depth probe and monitor the environment around the tube a substantial distance from the device.

The invention also resides in a method of removing an interior portion of a metal tube, characterized by the steps: (A) inserting into a metal tube to be sampled, a remotely operated diagnostic tube sampling device, for cutting through a portion of a metal tube wall for analysis, where the device contains an emitter and receiver of at least one of electromagnetic fields and ultrasonic waves, a cutting head with an associated motor, and a retrieval assembly to detach a cut wall portion; (B) moving the sampling device within the metal tube by a driving mechanism, while selectively emitting and receiving at least one of electromagnetic fields and ultrasonic waves by the sampling device to locate defects in a portion of the metal tube wall for analysis; (C) cutting a hole with the cutting head from the inside of the tube through the metal tube wall where defects were located, to provide a cut, removable metal tube wall portion containing defects and engaging the removable wall portion with the retrieval assembly to detach the cut metal wall portion; (D) removing such cut metal wall portion to leave a hole through the tube wall; and (E) moving the sampling device with the cut metal wall portion out of the tube by the driving mechanism.

This method also allows mounting the cut wall portion from the tube to be sampled onto a separate tube, for testing physical and mechanical properties of the cut wall portion. This method would retrieve a nearly distortion free sample which could be welded onto the wall of a surrogate testing tube to permit leak rate testing and burst testing. Preferably, a variety of visual devices or probes, or machining tools could be mounted on and extendable from the sampling device, or a separate associated or independent unit, to be inserted through the window opening in the tube wall to in-depth monitor the environment outside the tube, in the secondary side of the generator, and the condition of the support plates and tube sheets that surround or are associated With the tube.

This invention provides a robotic, diagnostic sampling apparatus and its method of use, to in-situ cut away a large interior section of a small metal tube with ease of retrieval, ease of subsequent testing on a surrogate tube, and ease of sleeving within the tube to close the hole through the tube wall. It provides a window, allowing, for example, a video probe to explore exterior tube conditions, as well as the condition of nearby support plates and tube sheets in the secondary side environment in a nuclear steam generator. The remote sample removal device, and associated window access diagnostic capabilities described herein, provide significant advantages over conventional tube pull technology. The procedure is cheaper, faster, less destructive and provides distortion-free samples which result in more reliable data and minimization of radiation exposure.

The method of this invention does not merely involve cutting through a tube wall at a predetermined location or a location determined by visual inspection through a video device, but involves diagnosis of tube problems, location of tube problems and capture of a full cut through tube sample. The method provides for detection of defects, flaws and faults in tube walls by selective use of, for example, ultrasonics or eddy current fields whereby, during rotational travel of a sampling device, measurements are performed and are analyzed to provide an assessment of an appropriate location where there is a wall flaw, and at which location to cut away part of the tube for sampling. This provides a window in the tube for further exploration, monitoring and probing of the exterior tube environment.

All aspects of the access window concept represent advantages over standard tube pull options. The ability to gather actual tubing samples at transition regions and then sleeve the tube for continued operation is a significant operational advantage. In addition, the remote sampling option is applicable to virtually any location along the straight length of tubing. For the case of nuclear steam generators, the remote sampling option produces much less radioactive waste product and, in turn, minimization of radiation exposure. Although the device is described herein primarily for use in steam generator and heat transfer components, it is useful in other applications including well casings where an electromagnetic and or ultrasonic means can be used to locate vessel wall anomalies.

BRIEF DESCRIPTION OF THE DRAWINGS

In order that the invention will be more clearly understood, convenient embodiments thereof will now be described, by way of example, with reference to the accompanying drawings, in which:

FIG. 3, is a block diagram of the method of this invention; and

FIGS. 4(A), 4(B) and 4(C) show a three dimensional view of the sequence involved in mounting a cut wall portion onto a separate testing tube for testing the cut wall portion.

DESCRIPTION OF THE PREFERRED EMBODIMENTS

Figure 1:
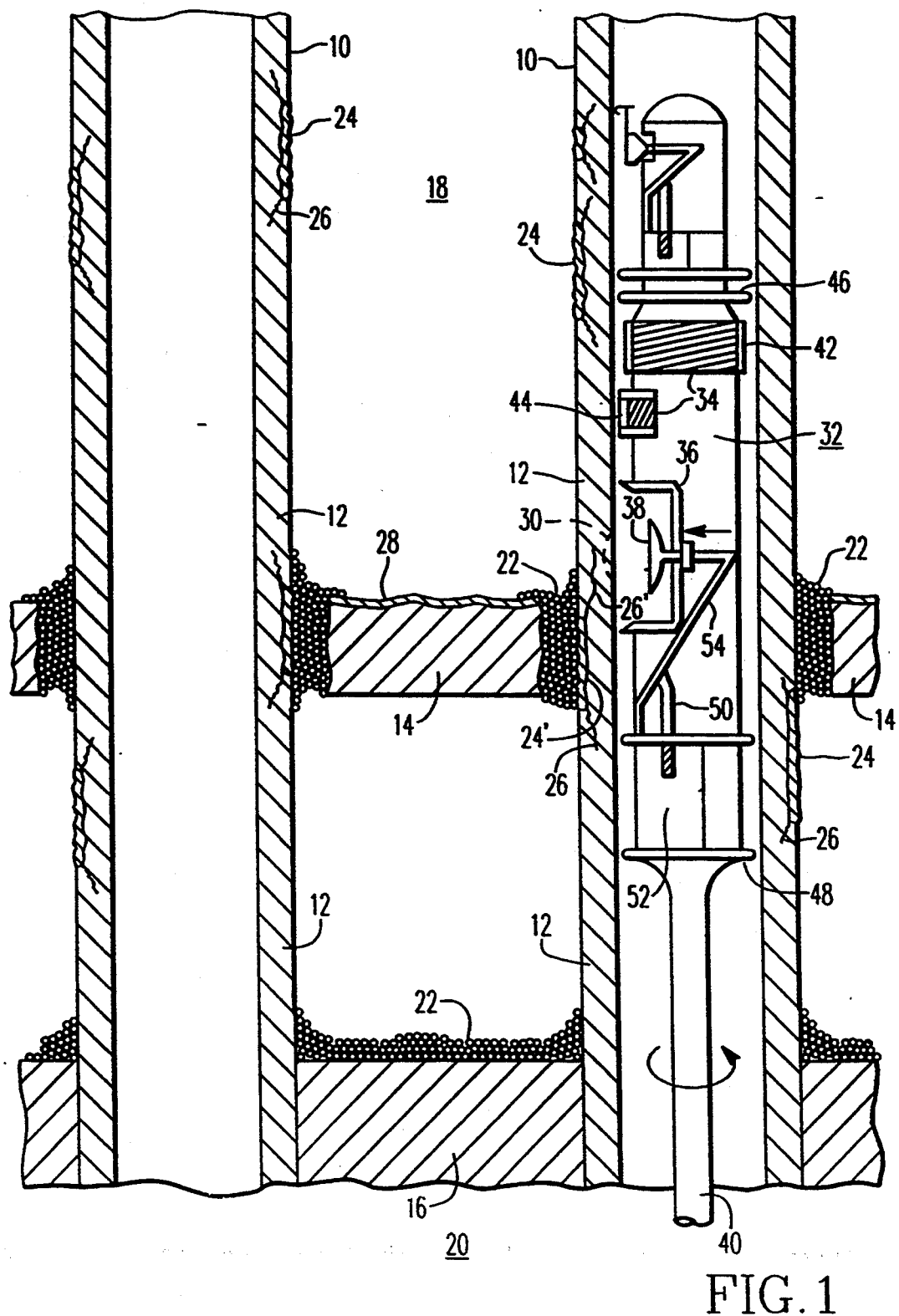
FIG. 1, is a view partially in section of a robotic sampling device driven into place, within a tube held by support plates and tube sheets, where a probe on the device has located a wall portion of interest having a defect, flaw or fault, and the cutting head is positioned to begin operation.

Referring now to FIG. 1, a tube 10 having tube wall 12 is shown, for example a heat exchanger tube in the secondary side of a steam generator. The tube can be disposed between support plates 14 and pass through tube sheet 16. The tube is metal, usually made from a corrosion-resistant alloy of iron, nickel and chromium and is up to about 10.2 cm (4 inches) in diameter and up to about 2.5 mm thick. The tube sheet is usually a low alloy steel, and the support plates can be either a low alloy steel or a stainless steel. As is well known in the art, nuclear steam generators contain three principal parts, including a secondary side 18, tube sheet 16, and a primary side 20 which circulates water heated from a nuclear reactor. The secondary side 18 of the generator includes the region or environment outside a plurality of small, metal heat exchanger tubes 10 (only a portion of which are shown in FIG. 1), as well as an inlet for admitting a flow of water. The inlet and outlet ends of the tubes are mounted in the tube sheet which hydraulically isolates the primary side of the generator from the secondary side.

Hot water flowing from the nuclear reactor is admitted into the section of the primary side 20 containing all of the inlet ends of the tubes. This hot water flows through these inlets, up through the tube sheet 16, and circulates within the tubes 10. This water from the reactor transfers its heat through the walls of the heat exchanger tubes 10 to the non-radioactive feedwater flowing through the secondary side 18 of the generator, thereby converting feedwater to nonradioactive steam which in turn powers the turbines of an electric generator. After the water from the reactor circulates through the tubes, it flows back through the tube sheet, through the outlets of the tubes, and into the outlet section of the primary side 20, where it is recirculated back to the nuclear reactor.

Over a period of time, sludge deposits consisting of magnetite, copper, copper oxides, nickel oxide, zinc oxide, aluminum compounds and other potentially corrosive chemicals may accumulate in various places including the annular spaces between the heat exchanger tubes and the tubesheet and support plates which surround them in the secondary side 18 of the generator. Despite the fact that the heat exchanger tubes are formed from a corrosion-resistant metal alloy, these corrosive chemicals, in combination with the hot water which flows around such tubes, may cause the remote possibility of a number of different flaws or defects in or on the tube walls including pinholes and various forms of corrosion degradation, one of which is intergranular stress corrosion cracking. If unchecked over a long period of time, such corrosion could ultimately result in the possibility of fissures or like defects in the walls of the tubes, which can cause the possibility of leakage of hot water from the nuclear reactor through the walls of those tubes into the secondary side 18 of the generator.

In greatly exaggerated form, magnetite and corrosive sludges are shown as deposits 22 in and around the tubes 10 and support plates 14, and on top of the tube sheet 16. Also shown in simplified form are tube corrosion defect sites 24 parallel to the longitudinal axis of the tubes, and stress cracks defects 26 within the tube walls 12. In some instances there may be very serious support plate corrosion as shown at site 28, completely outside the tubes 10. In order to check the magnitude of such degradation and cracks and other defects, it is necessary to use some sort of driven inspection sampling apparatus. Some prior art devices have removed very shallow inner portions, shown enlarged greatly in thickness by dotted line 30, but such methods would not sample parallel degradation such as at site 24' or stress cracks such as at site 26'.

The remotely operated, axially elongated, robotic diagnostic sampling device 32 of this invention, which is used to completely cut out a portion of the metal tube wall having a thickness on the order of from 0.75 mm to 2.5 mm, usually from 1.0 mm to 2.0 mm, and retrieve it for analysis is usually cylindrical, and basically contains a variety of probe means 34, to locate a defective tube wall portion of interest, a cutting means such as cutting head 36, an assembly 38 to provide a means to detach a sample, and a driving mechanism connection 40 to a driving means, not shown.

The sampling device 32 shown, which is a carrier for the probes 34, cutting head 36, and the like, would be rotatably mounted onto a main housing assembly that is inserted within the tube 10. The housing assembly would have one end which remains stationary during operation of the sampling device and an other end, which includes a cable housing proximate to the sampling device, which would rotate and advance or retract axially during operation. The cable housing would be connected to the sampling device by means of driving mechanism connection 40, and serves to move the sampling device along a helical path, as is well known in the art. Usually, a couplant or cooling fluid medium, such as regular water, is present inside the tube while the sampling device is in use.

The probe means 34 can include, for example a bobbin eddy current probe 42 which winds around the circumference of the sampling device 32, somewhat as shown in FIG. 1, and a spring loaded surface riding pancake eddy current probe 44, which is usually smaller and wound transverse to the axis of the sampling device 32. These probes could be operated, preferably, in the range of from 1 KHZ to 5 MHZ. One or more of these types of eddy current probes can be utilized, of various diameters, to emit various frequencies to detect defects at various depths within the tube wall.

This probe combination would serve as an inspection and diagnostic device as well as cutter position guide. Both utilize emission of an electromagnetic field, which is received and then recorded by an associated computer means/instrumentation means, to scan the tube walls 12 for any defects in the wall, locating the portion of the wall where sampling is desired. Both probes would usually be encased in self-lubricating plastic to protect the delicate coil windings and minimize any friction with the inside of the tube wall. The bobbin probe 42 provides generalized information about tube wall defects and the pancake probe 44 provides much more concentrated electromagnetic emissions which allow a more exact location of the flawed areas.

Each of the eddy current probes 42 and 44 are connected by way of cable and then lead wire to an external eddy current tester means, the output of which is connected to the input of an associated computer in order to interpret signals associated with the electromagnetic fields. Electromagnetic alternating fields could be induced into the tube walls, and with respect to amplitude could be detected at a distance from the introduction point and the phase displacement measured, to identify defects in the tube wall in order to interpret signals associated with the electromagnetic fields.

Alternating current conducted through the eddy current coil causes the coil to emanate a time-varying electromagnetic field which in turn induces eddy currents in the inner walls of the tube as the coil is moved axially. Because the eddy currents create a electromagnetic field that is opposite in polarity to the time-varying electromagnetic field emanated by the probe coil, the eddy currents generated in the tube apply a measurable impedance to the alternating current that fluctuates through the coil. Since defects in the tube wall create regions of variable resistance, eddy current probes may be used to locate defects by constantly monitoring the impedances of the coils as the probe coils are moved along the walls of the tube. A more complete description of such probes, and computer connections associated therewith can be found in U.S. Pat. No. 4,855,677, herein incorporated by reference.

Additionally, a variety of transducer shapes (not shown), located at the central axis of the sampling device or offset a predetermined distance from the central axis, can be used as ultrasonic probes on the sampling device, to, if desired, direct ultrasonic beams radially, chordally or axially from the sampling device, which radiated ultrasonic beams would be reflected and received by an appropriate device to generate data, as is well known in the art. These probes could be operated preferably, in the range of from 1 MHZ to 25 MHZ. These ultrasonic probes would each be connected to individual ultrasonic pulser-receiver means by a cable. The outputs of these pulser-receivers would be connected to the input side of the associated computer in order to interpret signals associated with the ultrasonic waves. An ultrasonic signal could be emitted and then reflected from the tube walls, and the time delay difference converted to a test signal for wall thickness, allowing a determination if wall thickness has been reduced due to corrosion and/or pitting. A more complete description of such probes, their operation, and computer connections associated therewith can be found in U.S. Pat. No. 4,856,337, herein incorporated by reference.

The driving mechanism to move the sampling device into the tube, rotationally within the length of the tube and out of the tube includes a motor connected to a source of electrical power and can have a helical drive train within the housing assembly mentioned previously, which is responsible for imparting a rotational movement, generally over 30° depending on the number of probe means on the sampling device, in order to scan the entire surface of the tube. The rotation can be a helical or screw-wise motion, or ±360° rotation about the central axis of the tube. This rotation is imparted to the cable housing which is connected to the sampling device. Thus, the sampling device is rotatably mounted on and helically movable with respect to the driving mechanism. The helical drive train can be formed from a co-linear arrangement of an electric motor, a gearbox, and an optical encoder. Shaft couplings can connect the input shaft of the optical encoder to the output shaft of the gearbox, and the output shaft of the encoder to the input shaft of a slip ring. The slip ring could allow the ultrasonic and eddy current probes to be connected to their various power sources despite the relative rotary movement between these probes, and the stationary drive train housing.

Optionally, slip rings, which sometimes pose reliability problems, could be eliminated if a ±360° back and forth rotation about the central axis of the tube is utilized rather than full continuous, screw type rotation. A variety of such driving mechanisms for tube sampling devices are well known in the art and further details with regard thereto can be found in U.S. Pat. No. 4,856,337, herein incorporated by reference.

Also shown on the sampling device 32, are centering discs 46 and 48 to help maintain the sampling device in concentric alignment with its axis of rotation within the tube 10. The driven cutting head 36 is preferably a preshaped elliptical electric discharge machining (EDM) electrode, movable to engage the tubing surface by the action of an axial push rod 50 energized by drive motor 52 and directed against a flat spring 54. The push rod would force the spring 54 towards the tube wall as shown by the arrow, causing the attached cutting head 36 to advance toward and contact the inside wall. When activated, the electrode would be supplied with electrical current to pierce the tube wall by electro erosion. This arrangement offers excellent cutting head position control and yet, optimum space for sample capture. Of course, other cutting head means such as mechanical trepan, water jet, laser, ultrasonic, and the like, and cutter control means such as air cylinder, electric solenoid, screw drive, and the like, with their associated electronics can be used, depending on the specific application. The couplant fluid usually present inside the tube such as regular water can be useful as a coolant in the cutting operation and to flush away any cuttings.

Thus, the cutting head or cutting means would engage the inside surface of the tube wall and pierce and cut into the tube wall, usually in a elliptical fashion, until the entire wall was penetrated and cut through with a cut line substantially transverse to the tube wall to usually provide a removable elliptical or circular disc type tube wall portion to be sampled. After removal of the sample, in all cases, there would be a hole completely through the tube wall, with removal of a whole wall portion rather than just a portion of the tube wall thickness.

A suction cup, such as a vacuum cup arrangement, can be used to capture the sample cut from the tube wall, and retraction of the EMD electrode carries the sample coupon into what would then be the delivery cartridge. Other capturing arrangements, such as clamps, magnets, a screw type bore, or the like, or the cutting head itself can be used as the retrieval assembly. Preferably, assemblies such as the vacuum cup or the like will fit compactly into the cutting head, forming a space saving delivery cartridge.

Figure 2:
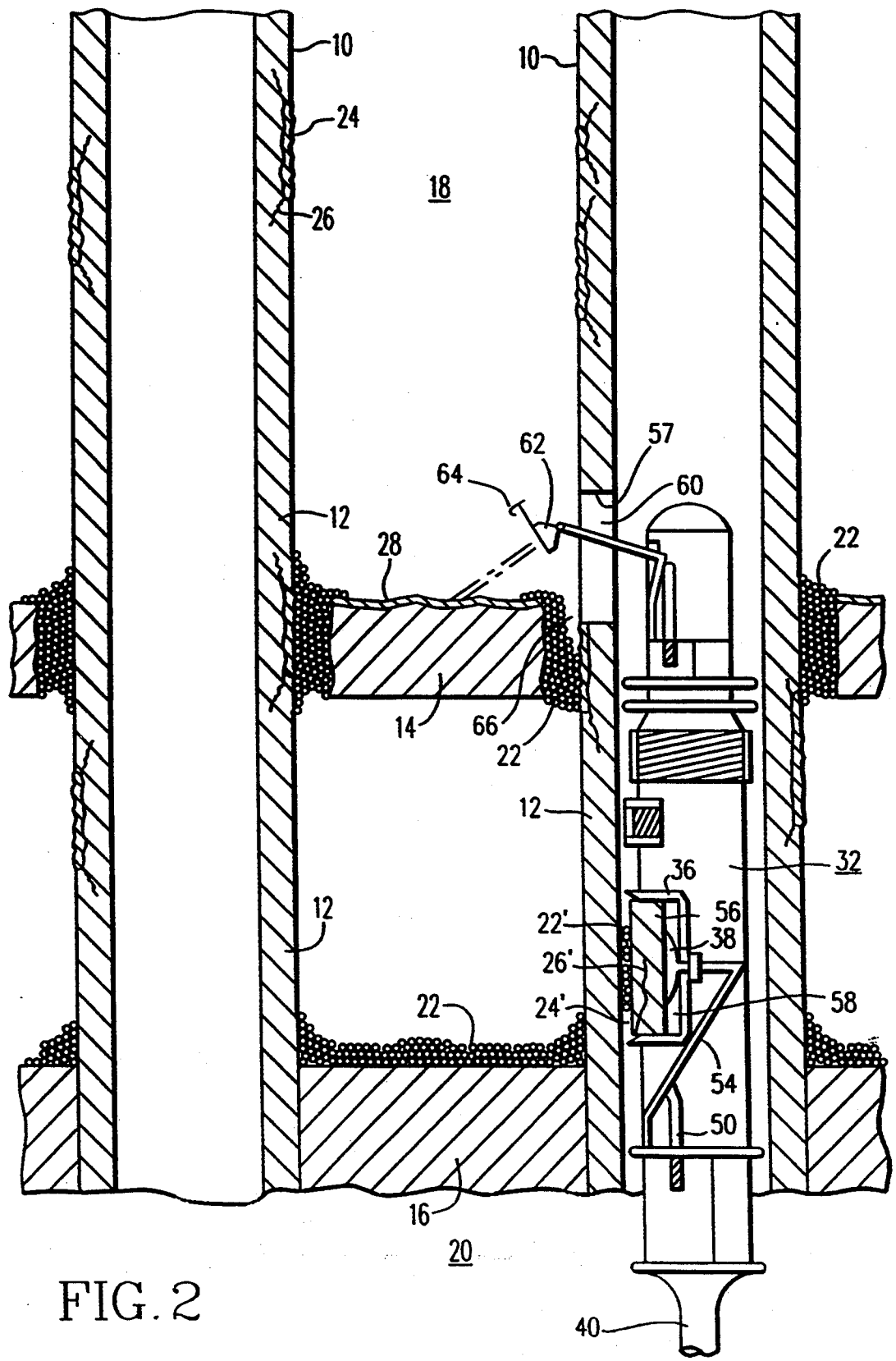
FIG. 2, which best shows the invention, is a view of the tube and device shown in FIG. 1 after the cutting head has cut a hole through the wall and a wall portion sample has been retrieved, where a video probe is inserted through the window opening.

Referring now to FIG. 2, the sampling device 32 is shown in a lowered position, after the assembly 38 has been used, in this case a suction cup, to remove or detach the sample cut wall portion 56 from the tube wall. As shown, the cut line 57 formed by the cutting head is substantially at a 90° angle to the inside tube wall surfaces allowing a large sample 56 to be cut away. Preferably, the suction device would engage the removable portion of the tube prior to cutting, so that the sample would not fall outside the tube when a support plate 14 was not present opposite the sample to be removed.

Thus, the sample 56 is shown removed and held by suction device 38 within the cutting head 36 in a delivery cartridge 58. The sample 56 is a large section of the tube wall. The hole or "window" 60 all the way through the tube wall allows additional exterior inspection in the vicinity of the tube by a variety of means. As can be seen, by removing an entire wall portion, exterior defects, such as degradation at site 24' or stress cracks such as at site 26' can be subsequently analyzed. Also, a substantial amount of sludge deposit 22' attached to the sample can also be retrieved and analyzed. As shown, the push rod 50 and spring 54 are in retracted position, similarly to FIG. 1 before cutting of the sample began.

FIG. 2 illustrates some of the inspection options associated with the "window" approach to heat exchanger maintenance. Examination of the environment external to tube 10, for example, the adjacent tube surfaces, flow holes, crevice deposits, and tube lanes, through the window 60 is possible. The sampling device 32, can have associated with it, means, such as probes, or additional devices extendable from the sampling device, and capable of passing through the hole to be cut in the tube to be sampled, and probing the environment a distance from the device. Such probes and the like can also be mounted on a separate device.

The means to probe the environment could be, for example a video probe, a scraper attachment or miniature machining tools such as drills, bores, insertion extensions to attach or to insert sensors, and the like. A telescoping video probe 62, preferably attached to and a part of sampling device 32, can be passed through the window 60 to look at and monitor the outside surface of the access tube and virtually any other region outside the tube where it is possible to position the probe. A scraper attachment tool 64 or the like, shown as part of the probing means, can also be used to collect sludge 22 or other deposits and retrieve them for analysis. While extremely valuable, visual examination of secondary side conditions is not the limit of the window concept.

Also, miniature machining tools attached to the sampling device 32 and based on existing technology can be used as part of the probing means to gather samples and install special sensors. For example, it is possible to scrape or trepan the crevice deposit in the support plate tube holes, at site 66, and retrieve them, to conduct an extensive subsequent chemical analysis. A small hole can be drilled through the support plate 14 to the crevice region 68 of an adjacent tube, and miniature electrochemical sensors installed to monitor crevice conditions under actual service operation. The sensor leads, either wire or fiber optics, can be routed through the window and out another window located at a convenient access port, where the signals can be monitored.

Other diagnostic sensors can be installed at various locations on the secondary side of the hardware. For example, strain gages and integrated thermal/radiation monitors are options, along with electrochemical probes for chemistry analysis. A significant advantage for access to secondary side components is the ability to install sensors on hardware that will not be impacted by tube plugging operations and associated changes in thermal loading. In addition to examination and sampling options, the window access concept permits the consideration of some unique remediation possibilities. For example, a corrosion prevention chemical or protective compound can be pumped from the sampling device to cover the top of a support structure such as on the support plate 14 at site 28, and fill or soak crevices. Also, in place, real-time experiments to evaluate remediation options can also be expedited with the window concept.

As an example of operation, following FIG. 3, a process of retrieval and sample analysis would include remotely delivering the diagnostic sampling device to the inside of a tube under investigation—step (A). The sampling device would be driven in a helical, screw—wise or ±360° back and forth rotational motion through the tube interior; resulting in helical scanning of the tube interior. The sampling device would contain an emitter and receiver of one or more frequencies of electromagnetic fields and/or ultrasonic waves and associated means for carrying out such emission and reception, a cutter head, a sample retrieval assembly and possibly one or more of a video probe, scraper means, drilling means and pumping means. Then, by emission and analysis of electromagnetic fields and/or ultrasonic waves by means of probes, detector means and various connected circuit means, programmed computers, selected computer graphics and displays and associated electronics, as the sampling device is moving, the sample area of interest would be located—step (B).

The data generated by the ultrasonic and eddy current probes would be correlated for each section of the tube and displayed simultaneously to the system operator to provide a determination of where defects are in order to sample. In step (C) the sampling device would be locked in place, the cutter head would be indexed to the target area, the retrieval assembly would be engaged to the target area, the cutter head would be started by an associated motor or electrical source, and a hole would be begun and then cut from inside the tube and straight through the tube, to provide a removable tube wall portion to be sampled, which tube wall portion could have any number of shapes depending on the type cutter head used and other testing requirements.

Then, in step (D), the vacuum or other type retrieval assembly would detach the cut wall portion to provide a window completely through the tube wall. The sampling device would then be moved out of the tube with the captured sample—step (E). The sample would then be mounted onto a separate tube or the like to test for deposit analysis, tension and bend tests, leak rate and burst tests, microcharacterization and other physical and mechanical properties—step F.

FIG. 4(A) shows how cut out and retrieved tube wall sample 56, containing stress crack defect at site 26', can be placed on a surrogate testing tube 72 made of the same material as the sample, then attached by laser welds 74 or the like, FIG. 4(B), and then tested for burst strength or the like, FIG. 4(C). As seen, pressurized air or the like can be fed through surrogate tube 72, and the amount of pressure to cause fracture, or actual bursting to provide gap 76 can be determined.

A number of options exist for closing the window in the tube after condition monitoring. The tube can be plugged by standard methods involving a permanent or removable plug. This option removes the tube from service. A more rational option would involve sleeving the window area of the access tube. A removable sleeve would permit periodic re-examination of the window access area resulting in improved time based diagnostic capabilities.

We claim:

1. A remotely operated diagnostic tube sampling device, movable within a metal tube to be sampled, comprising:
    (A) An emitter and a receiver of at least one of electromagnetic fields and ultrasonic waves, capable, when inserted in a metal tube to be sampled, of locating defects in the metal tube wall;
    (B) a cutting head capable of cutting a hole completely through said metal tube to provide a sample;
    (C) a retrieval assembly capable of engaging said sample portion and detaching it;
    (D) a probing means extendable from the device, and capable of passing through the hole to be cut in the tube to be sampled, and probing the environment around the device;
    (E) an instrumentation means to receive and interpret signals associated with the electromagnetic fields or ultrasonic waves; and
    (F) an associated driving mechanism capable of moving the sampling device within the tube length.

2. The sampling device of claim 1, containing at least one eddy current probe capable of emitting electromagnetic alternating fields, and where the driving mechanism is capable of moving the sampling device rotationally within the tube length.

3. The sampling device of claim 1, where the sampling device is cylindrical and the cutting head is an electric discharge machining electrode, movable by a push rod energized by a motor.

4. The sampling device of claim 1, where the retrieval assembly contains a suction cup.

5. The sampling device of claim 1, where the retrieval assembly contains a suction cup and the assembly is contained within the cutting head.

6. The sampling device of claim 1, where the probing means comprises a video probe.

7. The sampling device of claim 1, where the probing means contains extendable tools capable of passing through the hole to be cut, to collect samples or install sensors in the environment.

8. The sampling device of claim 1, rotatably mounted on and helically movable with respect to the driving mechanism, to enable the emitters and receivers to scan the inside of the tube to locate defects.

9. The sampling device of claim 1, where the driving mechanism includes a motor connected to a source of electrical power for rotating the sampling device.

10. The sampling device of claim 2, also containing at least one transducer capable of emitting ultrasonic waves.

11. A method of removing, an interior portion of a metal tube, comprising the steps:

(A) inserting into a metal tube to be sampled, a remotely operated diagnostic sampling device, for cutting through a portion of a metal tube wall for analysis, where the device contains an emitter and receiver of at least one of electromagnetic fields and ultrasonic waves, a cutting head, and a retrieval assembly to detach a cut wall portion;

(B) moving the sampling device within the metal tube by a driving mechanism while selectively emitting and receiving at least one of electromagnetic fields and ultrasonic waves by the sampling device, to locate defects in a portion of the metal tube wall for analysis by means of an instrumentation means to receive and interpret signals associated with the electromagnetic fields or ultrasonic waves;

(C) cutting a hole with the cutting head from the inside of the tube through the metal tube wall where defects were located to provide a cut, removable metal tube wall portion containing defects and engaging the removable wall portion with the retrieval assembly to detach the cut wall portion;

(D) removing such cut metal wall portion to leave a hole through the tube wall;

(E) examining the environment external to the cut tube by a probe through the hole;

(F) inserting sleeving inside the tube to cover and close the hole through the tube wall; and (G) moving the sampling device with the cut metal wall portion out of the tube by the driving mechanism.

12. The method of claim 11, where the sampling device contains at least one eddy current probe capable of emitting electromagnetic alternating fields, a suction cup retrieval assembly, and an associated computer to interpret signals associated with the electric fields or ultrasonic waves, and the sampling device is moved in a rotational movement within the metal tube.

13. The method of claim 11, where the sampling device is rotatably mounted on and helically movable with respect to the driving mechanism, and a final step includes mounting the cut wall portion from the tube to be sampled onto a separate tube, for testing physical properties of the cut wall portion.

14. The method of claim 11, where an extendable video probe is passed through the hole in the tube wall of the tube to be sampled, to probe the environment of regions outside the tube a distance from the device.

15. The method of claim 11, where the tube is surrounded by support plates and tube sheets and where an extendable video probe is passed through the hole in the tube to probe the condition of the support plates and tube sheets.

16. The method of claim 11, where the tube is surrounded by support plates and tube sheets having deposits thereon, and where extendable tools are passed through the hole in the tube to collect samples of the deposits or install sensors on the support plates or tube sheets.

17. The method of claim 13, where, the cut wall portion is mounted onto a surrogate tube and submitted to leak rate and burst testing.

* * * * *